United States Patent [19]

Valerio

[11] Patent Number: 4,892,529
[45] Date of Patent: Jan. 9, 1990

[54] METHOD OF AUTOLOGOUS TRANSFUSION

[75] Inventor: Michael A. Valerio, Wallingford, Conn.

[73] Assignee: Sherwood Medical Company, St. Louis, Mo.

[21] Appl. No.: 268,666

[22] Filed: Nov. 4, 1988

Related U.S. Application Data

[63] Continuation of Ser. No. 923,058, Oct. 24, 1986, abandoned.

[51] Int. Cl.⁴ ............................................. A61M 1/00
[52] U.S. Cl. ................................... 604/317; 604/319; 604/4
[58] Field of Search .............................. 141/382–384; 128/DIG. 24; 285/921, 355, 390; 604/4, 5, 408–410, 262, 317–320, 414, 415, 905

[56] References Cited

U.S. PATENT DOCUMENTS

| | | | |
|---|---|---|---|
| 3,872,868 | 3/1975 | Kline | 128/DIG. 24 |
| 4,033,345 | 7/1977 | Sorenson et al. | 604/4 |
| 4,047,526 | 9/1977 | Reynolds et al. | 604/4 |
| 4,439,190 | 3/1984 | Protzman et al. | 604/319 |
| 4,540,413 | 9/1985 | Russo | 604/320 |
| 4,767,417 | 8/1988 | Boehringer et al. | 604/31 |
| 4,781,707 | 11/1988 | Boehringer et al. | 604/317 |

OTHER PUBLICATIONS

"Pleur-Evac Auto Transfusion System", Deknatel Division, Pfizer Hospital Products Group, 110 Jericho Turnpike, Floral Park, N.Y. 11001, Jan. 1986.

Primary Examiner—Jerome L. Kruter
Attorney, Agent, or Firm—Andrew J. Beck; Montgomery W. Smith; Richard D. Allison

[57] ABSTRACT

A transfer bag apparatus is disclosed which is adapted to be used in the autologous transfusion of blood to a patient by collecting the blood from the collection bottle of a drainage device for the chest cavity of the patient. The transfer bag comprises a flexible bag, having means at one end of the bag to be placed in fluid communication with an infusion set to transfuse the patient with blood, and means at the other end of the bag adapted to be placed in fluid-tight communication with the interior of the collection bottle to transfer blood to the interior of the blood bag. The method of autologously transfusing a patient by means of the present invention involves collecting blood in the collection bottle, placing the transfer bag assembly in communication with the blood in the collection bottle, transferring the collected blood from the collection bottle to the transfer bag, and allowing the blood collected in the transfer bag to be infused into the patient.

6 Claims, 2 Drawing Sheets 4,892,529

METHOD OF AUTOLOGOUS TRANSFUSION

This is a continuation of co-pending application Ser. No. 923,058 filed on Oct. 24, 1986 now abandoned.

BACKGROUND OF THE PRESENT INVENTION

1. Field of the Invention

The present invention relates to the autologous transfusion of blood to a patient from the collection bottle of a drainage device for the chest cavity of the patient by means of a transfer bag apparatus.

2. Description of the Prior Art

It is known to collect fluid, blood and gases from the chest cavity between the lung and the surrounding rib cage of a patient by using an underwater drainage device having a liquid seal which permits gases and liquid to be removed from the patient's chest cavity but which prevents the flow of gases back to the chest cavity. U.S. Pat. No. 4,439,190 to D. E. Protzmann et al., which is incorporated herein by reference, describes such collection systems and specifically relates to an improved "three-bottle" collection system. As used herein, the term "collection bottle" is intended to cover the type of collection bottle or chamber shown in the Protzmann et al. patent. The collection bottle in the Protzmann device is detachable containing a bayonet-type, male screw top configuration adapted to be placed in fluid-tight communication with a manifold in the device.

U.S. Pat. No. 4,006,745 describes an autologous transfusion system and method which contemplates the use of a flexible transfer bag which functions to receive blood from a second receptacle in a dual receptable blood-receiving apparatus. There is no suggestion of using the transfer bag with the type of collection bottle shown in the Protzmann patent. Also, the transfer bag shown in this patent differs from the bag of the present invention since it has a single opening or puncture site to both receive blood from the receptacle as well as later serve as a point of attachment for a transfusion set. This puncture site is not designed or adapted to be placed in fluid-tight communication with type of collection bottle shown in the Protzmann patent.

U.S. Pat. No. 3,866,608 illustrates, in Fig. 5, for example, a suction collection system which utilizes a lower blood reservoir bag made of flexible material which contains two openings to receive blood from an upper reservoir and to connect to an infusion set, respectively. The inwardly projcting sleeve in this bag which is adapted to receive an extending tube from an upper collection reservoir is, again, not designed or adapted to be placed in fluid-tight communication with the type of collection bottle shown in the Protzmann patent.

SUMMARY OF THE PRESENT INVENTION

The present invention relates to a transfer bag apparatus which is adapted to be used in the autologous transfusion of blood to a patient by collecting blood from the type of collection bottle shown in the Protzmann patent. The transfer bag of the present invention comprises a flexible blood bag having means at one position thereon which are adapted to be placed in fluid-tight communication with an infusion set to thereby transfuse the patient with blood collected in the transfer bag from the collection bottle and with means at a separate position on the bag which are especially adapted to be placed in fluid-tight communication with the interior of the chest drainage collection bottle of Protzmann et al. to transfer blood collected in that type of collection bottle to the interior of the transfer blood bag.

The present invention also encompasses the combination of a detachable collection bottle from an underwater chest drainage device and the transfer bag apparatus.

The present invention, moreover, relates to a method of autologously transfusing a patient which comprises the collection of blood from the chest cavity of the patient into a collection bottle for an underwater chest drainage device, placing the transfer bag apparatus of the present invention in fluid-tight communication with the blood collected in the collection bottle, transferring the collected blood from the collection bottle to the transfer bag, and allowing the blood collected in the transfer bag to be infused into the patient by means of a conventional infusion set.

DESCRIPTION OF THE DRAWINGS

The present application will be further understood by reference to the Drawings which form a portion of the present specification wherein.

DETAILED DESCRIPTION OF THE PRESENT INVENTION

Figure 1:
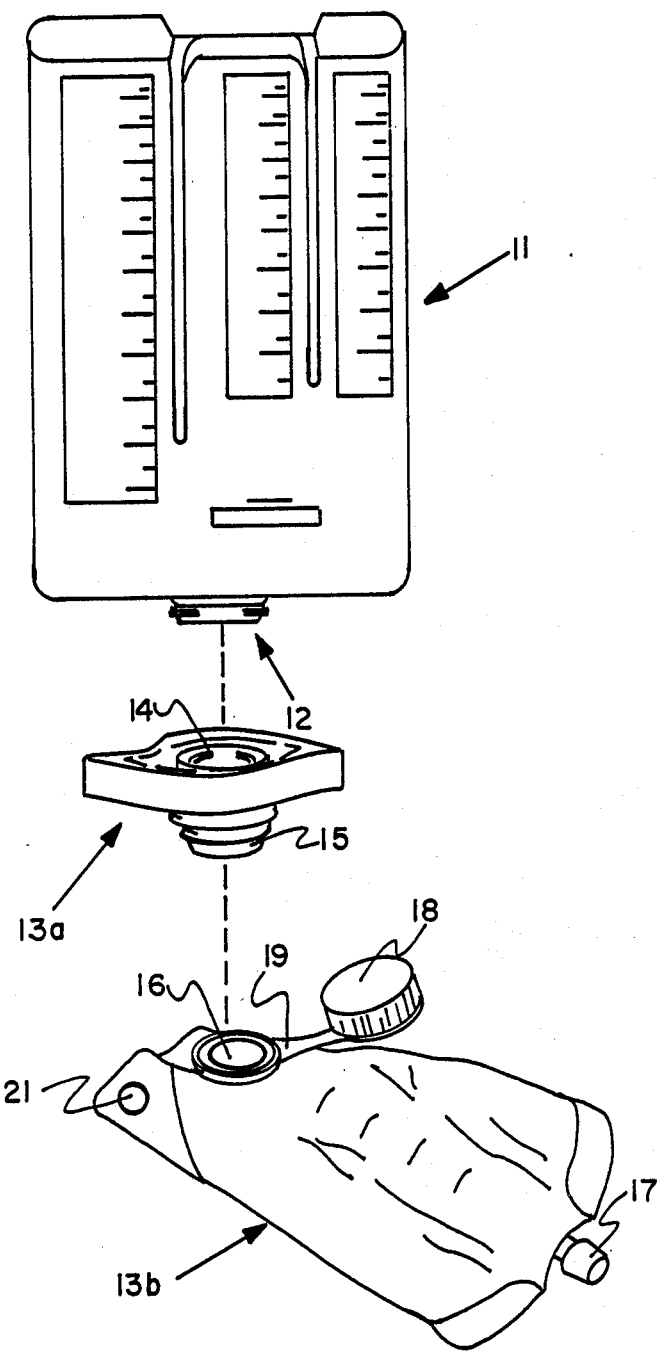
FIG. 1 is a perspective view showing the transfer bag apparatus of the present invention and the particular collection bottle of the device shown in the aforementioned U.S. patent to Protzmann et al.

FIG. 1 illustrates a collection bottle 11 of the type that is shown in U.S. Pat. No. 4,439,190, which is incorporated herein for its teaching regarding the construction of such a detachable collection bottle. As can be seen from the Drawing, the collection bottle has an outlet opening 12 with bayonet-type ridges on its neck which are described in the aforementioned patent as being especially adapted to engage cooperating lugs on a manifold in the collection device (not shown) in order to assure a fluid-tight connection.

The transfer bag apparatus of the present invention shown in FIG. 1 comprises a bottle cap component 13(a) as well as an infusion blood bag 13(b). In order to insure a fluid-tight communication between the outlet opening 12 of bottle 11 and the blood bag 13(b), it is essential that means be provided (e.g., female screw cap means, snap-fit means, or gasket means) which appropriately mate with the male screw top means on outlet 12 to effectuate a proper fluid-tight seal. The bottle cap 13(a) in a preferred embodiment has a threaded screw cap member 14 which is especially adapted to mate with the ridges contained on the screw top outlet neck 12 on the collection bottle 11 so as to form a fluid-tight seal. On the other side of the bottle cap 13(a) is a male snap-fit closure member 15 which is adapted to engage with a female cooperating snap-fit closure opening 16 on one end of infusion blood bag 13(b).

The infusion blood bag is preferably formed of a flexible polymer material and preferably has at an end remote from the snap-fit closure 16 a spike port/cover assembly 17 which can be placed in fluid-tight communication with a conventional infusion set (not shown) to infuse blood collected in the infusion blood bag from the collection bottle. Preferably, a blood filter material can be placed inside blood bag 13(b) so that blood from the collection bottle 11 will pass through the filter as it drains into the blood bag 13(b). The spike port/cover assembly 17 is preferably a two-component assembly with the cover keeping the spike port sterile until it is attached to the tubing set. As shown in FIG. 1, the transfer blood bag also includes a closure plug/cover component 18 joined to the snap-fit closure 16 by means of a flexible connecting member 19. The closure plug/cover component 18 is also a two component system with the cover serving to keep the closure plug sterile. The cover is removed prior to insertion of the closure plug into snap-fit closure 16. This closure plug allows for closure of the infusion blood bag after it has been used to collect blood from the collection bottle 11.

Figure 2:
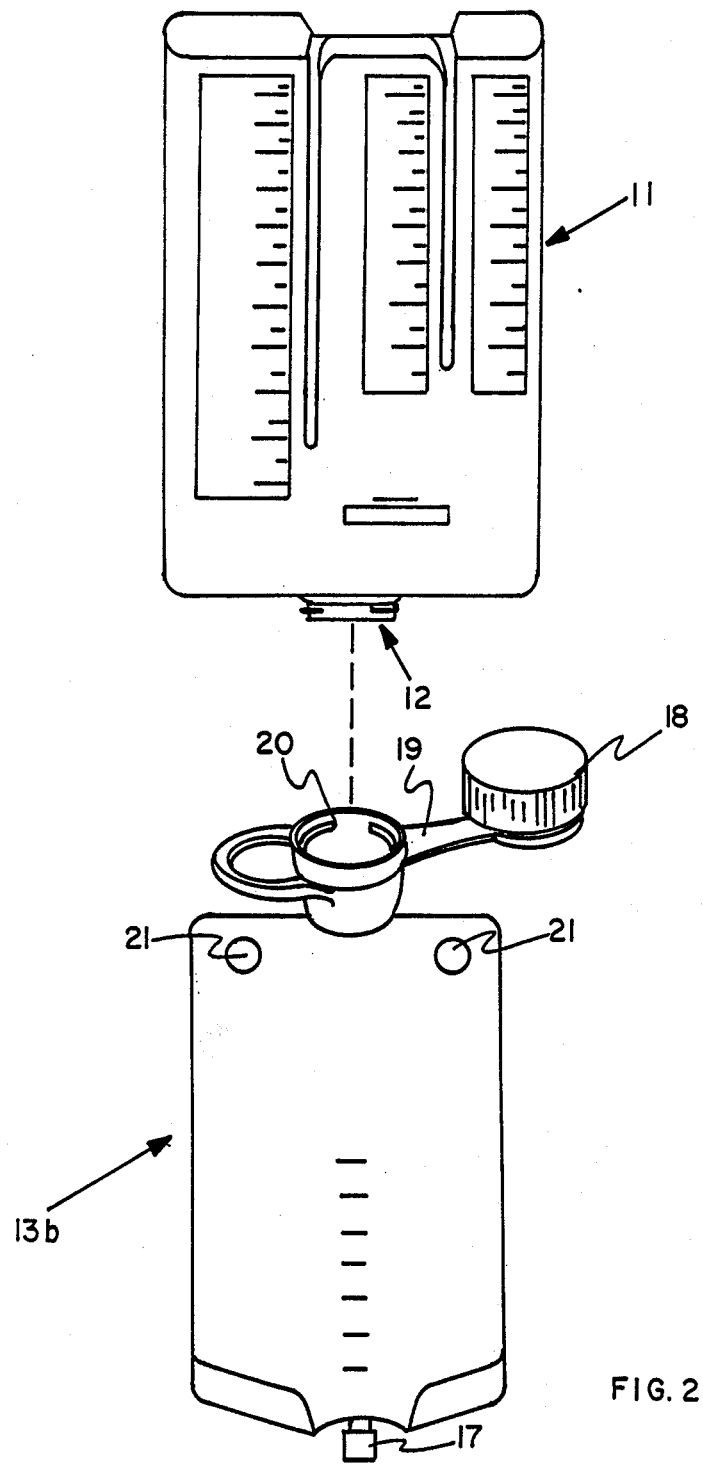
FIG. 2 is a perspective view of another embodiment of the transfer bag apparatus which is especially adapted to be used with the type of collection bottle shown in FIG. 1.

FIG. 2 shows an alternative embodiment to the type of transfer bag shown in FIG. 1 with the exception that the bottle cap 13(a) has been eliminated with placement of a cooperating female closure 20 on one end of the bag itself, rather than in the type of discrete bottle cap 13(a) component shown in FIG. 1. Otherwise, the two embodiments function quite similarly.

In order to utilize the transfer bag apparatus shown in FIGS. 1 and 2, the person of ordinary skill in the art would first collect blood from the chest cavity of a patient into the collection bottle in the type of drainage device described before. Once this has been accomplished, the collection bottle is removed from the drainage device and is readied for being placed in fluid communication with the transfer bag assembly shown in either FIGS. 1 or 2. The embodiment shown in FIG. 1 requires that the bottle cap 13(a) be affixed to the outlet opening 12 of the collection bottle, followed by the mating of the snap-fit closure members 15 and 16 to place the collection bottle and the transfer bag 13(b) in secure fluid-tight communication to allow for transfer of blood from the collection bottle 11 to the blood bag 13(b) without spilling. Preferably, the transfer bag 13(b) is preassembled to bottle cap 13(a) and is packaged in that configuration for later use. The blood is thereafter transferred to the blood bag 13(b). Once the blood is transferred from the collection bottle 11 to the transfer bag 13(b), the bag is removed from the bottle cap 13(a). The cap 13(a) remains attached to the collection bottle 11. The sterile cover is removed from the closure plug. The closure plug is inserted into the closure opening 16 on the bag 13(b). The sterile cover from the closure plug is used to close the opening in the cap which is on the bottle. This serves to close the bottle and prevent blood spillage. At this point, the infusion blood bag contains the blood in a sealed bag ready for later transfusion. The transfusion can take place by appropriately suspending the blood bag via hole 21 on an appropriate transfusion stand and thereafter connecting a suitable infusion set to the spike port contained at the other end of the bag after removal of the cover. The Drawings show the spike port with the cover covering it and designates this combination with reference numeral 17.

The foregoing has been presented to illustrate certain embodiments of the present invention, but should not be construed in a limiting sense. The scope of protection that is sought is set forth in the claims which follow.

I claim:

1. A method of autologously transfusing a patient which comprises:
    (a) collecting blood from the chest cavity of the patient in the collection bottle of an underwater drainage device for the chest cavity;
    (b) detaching the collection bottle from the underwater drainge device;
    (c) placing in fluid-tight communication with the blood collected in the collection bottle, a transfer blood bag having first and second ends and a means at the second end thereof to be placed in fluid-tight communication with an infusion set for the patient;
    (d) transferring the collected blood from the collection bottle to the transfer bag through the first end of said transfer bag; and
    (e) allowing the blood collected in the transfer bag to be infused into the patient through the infusion set.

2. A method of autologously transfusing a patient which comprises:
    (a) collecting blood from the chest cavity of the patient in the collection bottle of an underwater drainage device for the chest cavity;
    (b) detaching the bottle from the drainage device at an outlet of the bottle adapted to be placed in fluid-tight communication with the drainage device;
    (c) attaching a transfer blood bag having first and second ends in fluid-tight communication with said collection bottle at said bottle outlet;
    (d) inverting said collection bottle following said attaching step;
    (e) transferring the blood within said collection bottle into said first end of said transfer bag by gravity flow;
    (f) connecting an infusion set to the second end of said transfer bag; and
    (g) infusing blood from the transfer bag through the infusion set into a patient.

3. A method as claimed in claim 2, additionally comprising: (f) filtering the blood during said transfusing step.

4. A method of autologously tranfusing a patient which comprises:
    (a) collecting blood from the chest cavity of the patient in an upright collection bottle of an underwater drainage device for the chest cavity;
    (b) unscrewing cooperatively engaged threaded members on the bottle and drainage device adapted to place the bottle in fluid-tight communication with the drainage device,
    (c) detaching the collection bottle in an upright orientation to avoid spoilage of blood therein, from fluid-tight communication with the drainage device;
    (d) a transfer blood bag having first and second ends thereon;
    (e) screwing a threaded member on the first end of said transfer blood bag into cooperative engagement with the threaded member of said collection bottle so that the bottle is in fluid-tight communication with said transfer bag;
    (f) inverting said collection bottle;
    (g) transferring blood from said collection bottle by gravity flow into said transfer bag;
    (h) connecting an infusion set in fluid-tight communication with said second end of said transfer bag; and
    (i) infusing blood from said transfer bag through said infusion set into the patient.

5. The method as claimed in claim 4, additionally comprising, following said transferring step;
    (j) unscrewing said threaded members of said collection bottle and said first end of said transfer bag;
    (k) detaching said transfer bag from fluid-tight communication with said collection bottle; and (l) screwing a threaded cap into cooperative engagement with the threaded member of said transfer bag so that the transfer bag threaded member is fluidly sealed.

6. A method of autologously tranfusing a patient which comprises:
  (a) collecting blood from the chest cavity of the patient in an upright collection bottle of an underwater drainage device for the chest cavity;
  (b) unscrewing cooperatively engaged threaded members on the bottle and drainage device adapted to place the bottle in fluid-tight communication with the drainage device,
  (c) detaching the bottle in an upright orientation to avoid spillage of blood therein, from fluid-tight communication with the drainage device;
  (d) screwing a threaded connecting member into cooperative engagement with the threaded member of said bottle and attaching a transfer blood bag in cooperative engagement with the connecting member, so that the bottle is in fluid-tight communication through said connecting member with said transfer bag;
  (e) inverting said bottle;
  (f) transferring blood from said bottle by gravity flow into said transfer bag;
  (g) connecting an infusion set in fluid-tight communication with said transfer bag; and
  (h) infusing blood from said transfer bag through said infusion set into the patient.

* * * * *